United States Patent [19] [11] 4,162,974
Pernic [45] Jul. 31, 1979

[54] DEAIRING AND RECIRCULATION SYSTEMS FOR DIALYSIS MACHINES

[75] Inventor: Stanley J. Pernic, Round Lake, Ill.

[73] Assignee: Baxter Travenol Laboratories, Inc., Deerfield, Ill.

[21] Appl. No.: 787,753

[22] Filed: Apr. 15, 1977

[51] Int. Cl.² ............................................. B01D 31/00
[52] U.S. Cl. .................................. 210/120; 210/128; 210/135; 210/136; 210/321 B; 55/170
[58] Field of Search ................... 55/170; 210/22, 32 B, 210/96 M, 85, 87, 436, 321 B, 134, 136, 135, 120, 128

[56] References Cited

U.S. PATENT DOCUMENTS

| | | | |
|---|---|---|---|
| 2,061,517 | 11/1936 | Kenny | 55/170 |
| 2,228,401 | 1/1941 | Pressler | 55/170 |
| 3,359,708 | 12/1967 | Barber | 55/170 |
| 3,669,880 | 6/1972 | Marantz et al. | 210/22 |
| 3,722,680 | 3/1973 | Smith | 210/321 B X |
| 3,827,561 | 8/1974 | Serfass et al. | 210/436 X |

*Primary Examiner*—Frank A. Spear, Jr.
*Attorney, Agent, or Firm*—Paul C. Flattery; Gerald S. Geren

[57] ABSTRACT

There is disclosed herein a deairing system for use in a bedside-console-type dialysis machine.

The system includes a selectively adjustable flow controller, a deairing tank, and a suction pump for drawing dialysis solution from the flow controller through the deairing tank and to the pump. The pump is also connected to the deairing tank for applying a negative pressure and for removing gas from the dialysis solution.

The tank is provided with a baffle-and-ball-type check valve arrangement for preventing flow of dialysis solution through the gas line. A recirculation loop is provided in conjunction with the pump and includes an air separation tank downstream of the pump and a negative pressure valve which connects the upstream side of the pump and recirculation tank. The air separation tank cooperates with the pump to assure efficient operation of the pump by minimizing the air drawn through the recirculation loop and to the pump from the separation tank.

8 Claims, 2 Drawing Figures

DEAIRING AND RECIRCULATION SYSTEMS FOR DIALYSIS MACHINES

BACKGROUND OF THE INVENTION

This invention relates to dialysis machines, and more particularly, to deairing systems for use in dialysis machines of the type known as bedside consoles.

In dialysis, a patient's blood and dialysis solution flow through a dialyzer which includes a semipermeable membrane for separating the blood and the dialysis solution. Impurities from the blood cross the membrane and enter the dialysis solution for disposal.

In some dialyzers the dialysis solution is drawn through the dialyzer under a negative pressure (i.e., below atmospheric pressure). The reduction of the pressure on the dialysis solution to below atmospheric pressure allows dissolved gas to come out of solution and form bubbles. If such bubbles enter the dialyzer, they can undesirably impair the efficiency and operation of the dialyzer.

Degassing or deairing systems are known for removing gas from the dialysis solution prior to dialysis. In U.S. Pat. No. 3,598,727 there is shown a central delivery system in which the dialysis solution is prepared and degassed at a central location and then delivered to multiple remote stations. The remote stations means. includes a dialyzer and an apparatus known as a "beside console" which monitors and controls the operation of the dialyzer. A venturi is provided at the bedside console for drawing the dialysis solution through the dialyzer under a negative pressure.

The degassing portion of this system includes: a pump, a restriction, and an atmospheric pressure debubbling tank, all of which are located at the central station. No degassing is provided at the bedside console and the debubbling tank is operated only at atmospheric pressure.

It is one object of this invention to provide an economical and efficient degassing system for use in a bedside console.

Another type of dialysis machine is shown in U.S. Pat. No. 3,626,670. In that machine there is provided a single pump positioned downstream of the dialyzer for drawing solution therethrough and a chamber upstream of the dialyzer for deairing. The dialysis solution flows through the chamber and the pump applies a negative pressure to the chamber for deairing the solution. Thus, the single pump provides two functions. A series of fixed restrictions are positioned in the various fluid flow lines for controlling fluid flow therethrough. These fixed restrictions may undesirably limit the flexibility of the system. Furthermore, due to the use of fixed restrictions, the relationship between the degassing negative pressure and the negative pressure at the dialyzer may undesirably change with changes in flow rates under varying operating conditions. A fluid recirculation loop is also provided downstream of the dialyzer and in cooperation with the pump for controlling the negative pressure in the dialyzer to control the flow of fluids through the system. Air from the deairing chamber will undesirably recirculate through the loop to the pump which may reduce the efficiency and life of the pump.

It is a further object of this invention to provide a single-pump-type degassing system for use in a bedside console which is flexible in that it is adaptable for use under varying conditions and in which the relationship of degassing and dialyzer pressure will not undesirably change during operation and in which the efficiency and life of the pump are maximized.

These and other objects of the invention will become apparent from the following description and appended claims.

SUMMARY OF THE INVENTION

There is provided by this invention a negative-pressure-and-deairing system for use in a bedside console dialysis machine, which is flexible in use, the operating condition of which will not change under varying conditions, and which employs a single constant-speed pump for drawing dialysis solution through the dialyzer and for deairing. The system includes a selectively adjustable flow control valve, through which dialysis solution is drawn to a deairing tank. Gas, usually air, is withdrawn from the tank through the top thereof and deaired dialysis solution is drawn from the bottom of the tank through the dialyzer. The single constant-speed pump draws: (1) the gas from the tank; and (2) the dialysis solution from the tank through the dialyzer. With this arrangement the pressure at the top of the tank is always more negative than at the bottom due to the dialyzer resistance.

The deairing tank includes a ball-type check valve and baffle arrangement for minimizing dialysis solution loss from the tank through the gas line.

The pump is part of a recirculation loop which is provided: for controlling the negative pressure in the dialyzer; and assuring efficient operation of the pump, a stable negative pressure applied to the dialyzer and maximized pump life. The recirculation loop includes the pump, a downstream air separation tank, and a negative pressure control valve. The downstream side of the tank is connected to the upstream side of the pump through the valve and adjustment of the valve controls the negative pressure. The air separation tank enhances the efficiency of the pump and stability of negative pressure by minimizing air or gas drawn through the pump from the recirculation loop and thus assures optimum negative pressure control.

DESCRIPTION OF THE PREFERRED EMBODIMENT

Figure 1:
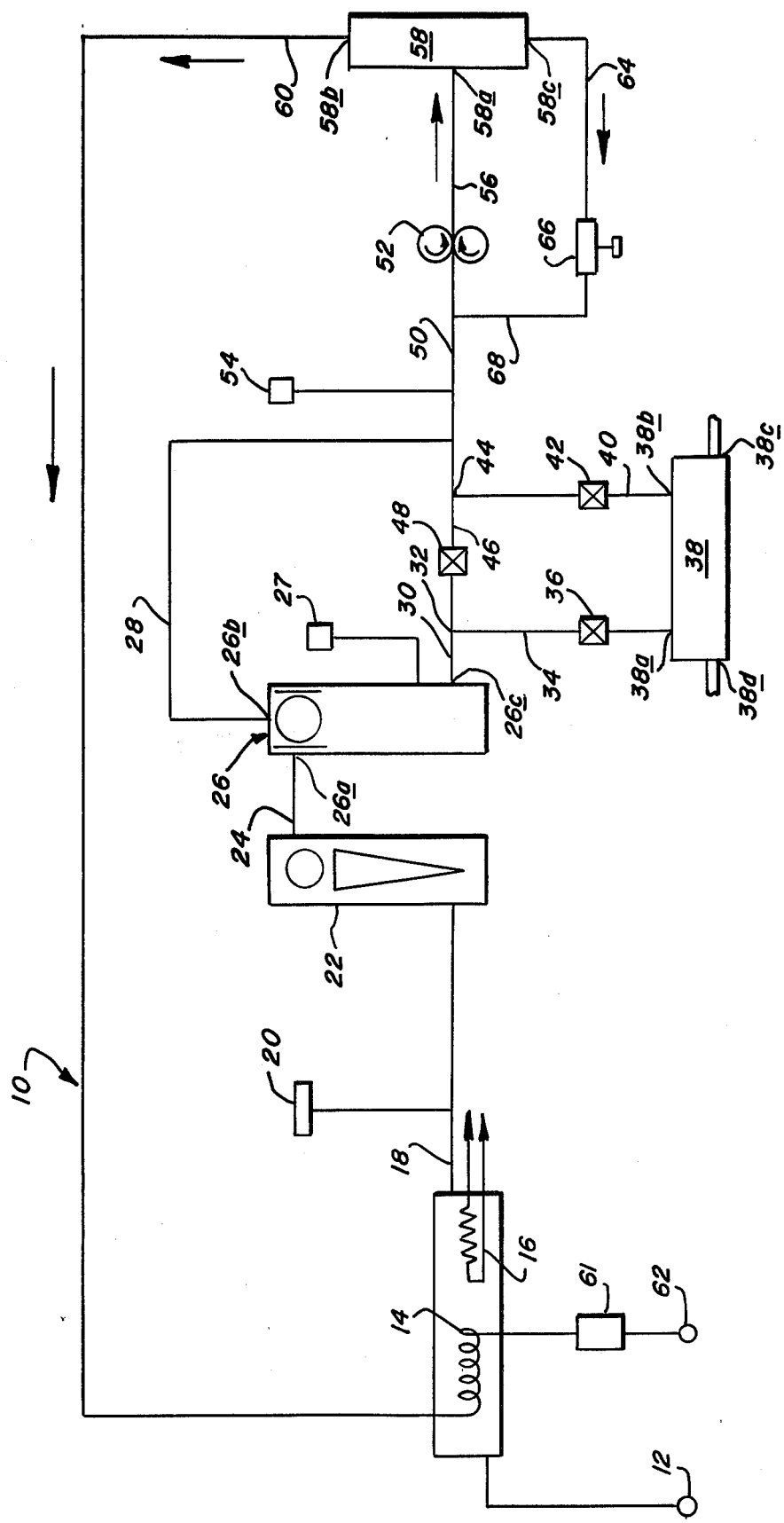
FIG. 1 is a flow diagram depicting the fluid flow path within the bedside console.

Referring now to the drawings, there is shown a flow path 10 generally which represents the flow of fluid through a bedside-console-type dialysis machine. Previously prepared dialysis solution enters the machine under a positive pressure through the inlet 12 and passes over heat exchanger coil 14 which initially warms the incoming dialysis solution. The solution then flows over thermostatically-controlled heater coils 16 for warming the solution to a final predetermined temperature. The solution flows from the heater coils 16 through a conduit 18, within which is positioned a heater-control thermostat 20 for sensing the solution temperature and for controlling the heater 16.

From the thermostat 20 the dialysis solution flows to a combined flow rate indicator and adjustable flow control valve 22. The valve is adjustable so as to permit control of the volume of dialysis solution drawn through the valve in relation to factors, such as patient size. The flow rates through the valve can vary between 200–600 ml/min.

The dialysis solution is drawn under a negative pressure from the valve 22 and into conduit 24. Due to the pressure change from positive to negative, gas or air which is dissolved in the dialysis solution separates and forms bubbles.

The separated bubbles and dialysis solution are drawn from the conduit 24 and into an upright elongated deairing tank 26. The deairing tank includes fluid inlet 26a, a gas outlet 26b, and a deaired dialysis solution outlet 26c. A temperature probe 27 extends into the tank 26 for sensing the dialysis solution temperature, prior to actual dialysis.

The gas bubbles are drawn through the outlet 26b and into line 28. Dialysis solution is drawn from the tank through outlet 26c via line 30 to the junction 32. The pressure at the gas outlet 26b is always more negative than at the dialysis solution outlet 26c.

Dialysis solution can be drawn from junction 32, through conduit 34 and shut-off valve 36 to a negative-pressure-type dialyzer 38. Negative pressure in the dialyzer may vary between about 0 and −400 mm Hg with −200 mm Hg being typical.

The dialyzer is provided with a dialysis solution inlet 38a and outlet 38b and a blood inlet 38c and outlet 38d. Spent or used dialysis solution exits the dialyzer via conduit 40, passes through shut-off valve 42 and flows to junction 44. A bypass line 46 connects the junctions 32 and 44, and the shut-off valve 48 controls the flow of dialysis solution through line 46.

During normal operation, valves 36 and 42 are open and bypass valve 48 is closed so as to direct dialysis solution through the dialyzer 38. In the event abnormal conditions occur, as for example if the sensor 27 detected an abnormally high temperature, valves 36 and 42 close and bypass valve 48 opens so as to prevent dialysis solution from flowing to the dialyzer and to direct flow through the bypass.

Line 50 connects junction 44 to the downstream or suction side of a positive displacement type suction pump 52 which operates at a substantially constant speed and at a substantially constant volume. The particular pump employed has a pumping capacity of about 1100 ml/min. The gas outlet line 28 is connected to line 50 downstream of junction 44 and upstream of pump 52. Thus the pump 52 operates to draw dialysis solution through the system from the flow control valve 22 and to draw gas from the deairing tank 26 through line 28.

A pressure transducer 54 is connected to conduit 50 upstream of the pump 52 to monitor the dialysis solution pressure, and in the event of abnormal pressures, the valves 36, 42 and 48 are operated to bypass the dialyzer.

Spent dialysis solution from line 40 and gas from line 28 are drawn through the pump 52 and flow under a positive pressure via line 56 to an air separation tank 58. The tank 58 includes a fluid inlet 58a, a drain outlet 58b, and a recirculation outlet 58c.

Dialysis solution and separated air flowing from the tank 58 flow through outlet 58b and the line 60 into the heat exchanger 14. The used dialysis solution is warm, and as it passes through the heat exchanger, it provides some heat for warming the incoming dialysis solution. The dialysis solution flows from the heat exchanger through a blood leak detector 61 to a drain outlet 62. In the event that abnormal conditions are detected here, the valves 36, 42 and 48 are operated to bypass the dialyzer 38.

Returning to the separation tank 58, a recirculation line 64 connects the outlet 58c to the upstream side of a manually adjustable negative pressure control valve 66. Another line 68 connects the downstream side of the valve 66 to the line 50 at a position upstream and on the suction side of the pump 52. The pump 52, tank 58 and valve 66 with the connecting lines 50, 56, 64 and 68 provide a recirculation loop whereby dialysis solution in the tank 58 can be recirculated through the pump 52. The volume of solution drawn from the tank 58 is dependent upon the flow rate through the valve 66.

The pump 52 pumps a constant or fixed volume of dialysis solution. The amount of fluid flowing through the pump is greater than the amount of fluid drawn through the dialyzer. In order to operate the pump efficiently, a quantity of spent dialysis solution, approximately equal to the difference between the flow rate through the control valve 22 and the capacity of the pump 52, is recirculated from the tank 58 to the pump 52. For example, the pump 52 requires approximately 1100 ml/min. in order to operate efficiently, and if the flow control valve 22 is set at 300 ml/min., approximately 800 ml/min. are recirculated.

By controlling flow through the negative pressure valve 66, the negative pressure between the flow control valve and pump 52 is controlled. If flow through the valve 66 is reduced, the negative pressure is increased (i.e., the difference between atmospheric pressure and actual pressure increases). This also means that the negative pressure in tank 26 and in line 28 increases, which, in turn, increases the effectiveness of the deairing system. In other words, the amount of air or gas removed from the dialysis solution varies in direct relation to changes in the negative pressure. This is desirable since the amount of gas which would come out of solution increases with increasing negative pressure, and if the amount of gas removed did not also increase, the effectiveness of the dialyzer could be impaired.

The air separation tank 58 is of a size and shape to enhance bubble separation and minimize bubble recirculation. Gas from line 28 and spent dialysis solution are delivered to the tank 58. The gas bubbles rise to the top of the tank for disposal along with some spent dialysis solution via line 60. Spent dialysis solution having a lower gas content is drawn from the bottom of the tank for recirculation. The recirculation of lower gas content dialysis solution enhances the efficiency and life of the pump 52 and stabilizes the negative pressure applied to the dialyzer. Furthermore, some gas separation may occur when the pump 52 draws spent dialysis solution through the valve 66. This separated gas will also rise to the top of tank 58, and thus the amount of gas in the recirculating dialysis solution is reduced to a minimum.

Figure 2:
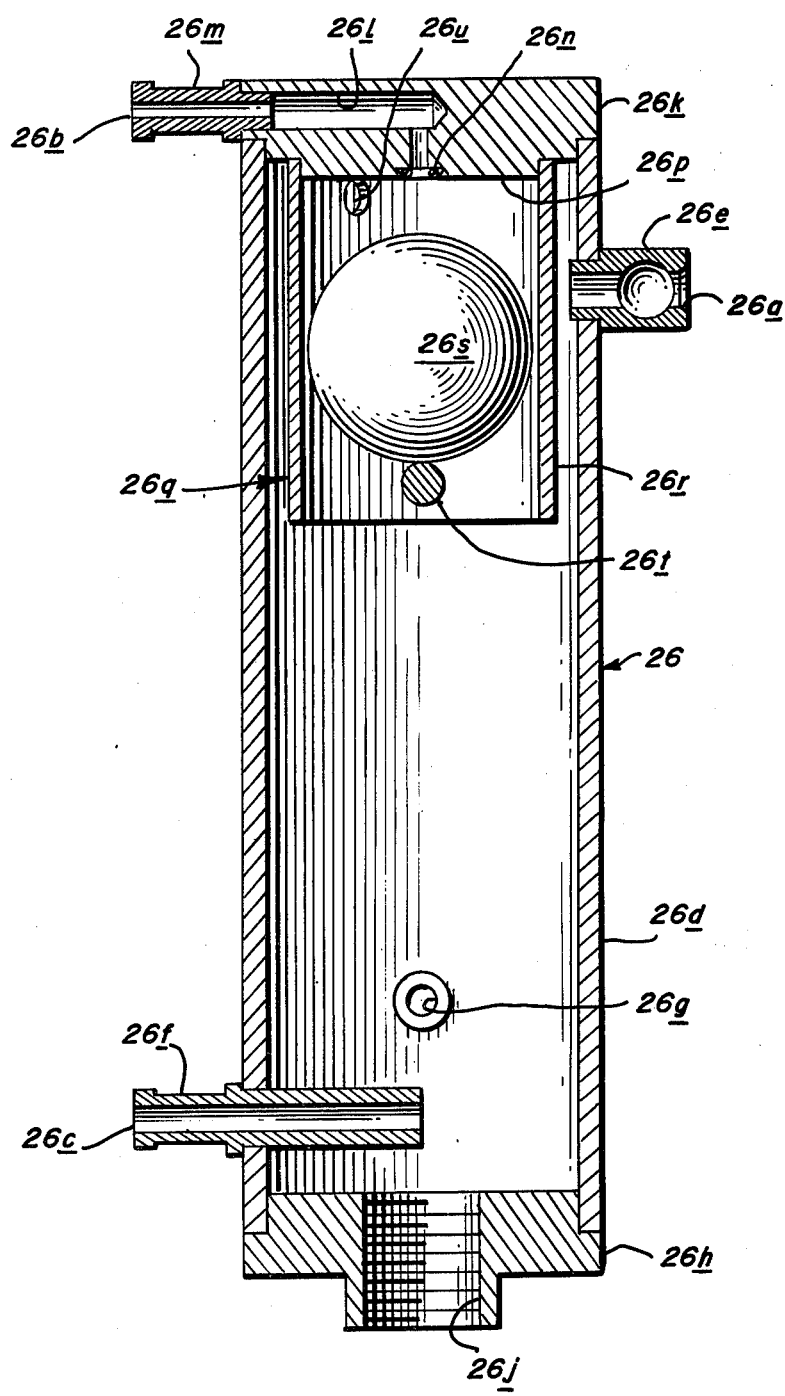
FIG. 2 is a vertical sectional view of the degassing tank.

Referring now to FIG. 2, the deairing tank 26 is shown. The tank is constructed from a cylindrical casing 26d into which extends an inlet nipple 26e which defines the inlet 26a and a dialysis solution outlet nipple 26f which defines the outlet 26c. The nipple 26f extends to the center of the casing. A small sealable opening 26g is provided through which the temperature probe 27 enters the casing. A bottom cap 26h closes the bottom of the casing and includes a clean out port 27j. A top cap 26k closes the top of the casing. The top cap is bored so as to define a gas passageway 26L from the tank interior to a nipple 26m which is fitted into the passageway and defines the outlet 26b. An O-ring 26n is provided at and about the entry to the gas passageway 26L.

The top cap also includes a boss-like structure 26p to which an internal baffle-and-check valve assembly 26q generally is mounted. The assembly 26q prevents flow of dialysis solution through the gas outlet, thereby assuring that the flow rate through the dialyzer 38 is the same as the flow rate through the indicator and valve 22. The assembly 26q includes a cylindrical baffle 26r which extends downwardly from the cap past the inlet 26a. A small annular space is left between the baffle and the casing 26d. A loose-fitting lightweight plastic ball-valve element 26s is positioned within the baffle and is held within the baffle by a pin 26t. In operation, when the tank is filled with dialysis solution or when the dialysis solution reaches a predetermined level, the ball 26s seats against the O-ring 26n preventing flow of dialysis solution through the passageway 26L. When the tank is not filled or the solution is below the predetermined level, the ball is spaced from the O-ring 26n, and the pump 52 can then draw gas from the tank and into a line 28. The separated air can flow upwardly within the baffle to the passageway 26L. Air which is trapped between the baffle 26r and the casing wall 26d flows through an opening 26u in the baffle wall to the passageway 26L.

It will be noted that the baffle 26r is interposed between the ball 26s and the inlet 26a. This positioning prevents incoming fluid from flowing directly against the ball and impairing its operation, as for example, by unseating the ball from a sealed position or by preventing the ball from seating against the O-ring 26n.

It will be appreciated that numerous changes and modifications can be made in the embodiments disclosed herein without departing from the spirit and scope of this invention.

What is claimed is:

1. A dialysis machine for drawing dialysis solution through a dialyzer under a negative pressure and for removing gas from the dialysis solution prior to delivery to the dialyzer, said machine including means defining a recirculation loop and negative pressure control for a dialyzer, said means positioned downstream of said dialyzer and comprising:

substantially constant speed and constant volume suction pump means positioned downstream of the dialyzer for removing gas and for drawing said dialysis solution through a dialyzer;

air separation and holding tank means positioned downstream of the pump means for receiving said removed gas and only spent-dialysis solution from a dialyzer, said tank means having an inlet, a drain outlet adjacent the top of the tank means, and a recirculation outlet adjacent the bottom of the tank means, and said tank means being shaped and constructed so as to permit gas and gas-containing spent-dialysis solution to exit said tank means through said drain outlet, and to permit spent-dialysis solution with a lesser gas content to be drawn from said tank means through said recirculation outlet; and negative pressure control valve means positioned downstream of the tank means, and cooperatively associated with said recirculation outlet and the upstream side of said pump means so that spent-dialysis solution having a lesser gas content is drawn from said tank means through said control valve means and recirculated directly to said pump 2. A dialysis machine as in claim 1, wherein said negative pressure control valve means is selectively adjustable so as to control the flow of spent-dialysis solution therethrough and to control negative pressure at a dialyzer.

3. A dialysis machine as in claim 1, which further includes conduit means for connecting the dialyzer to the pump means, the pump means to the tank means, the tank means to the valve means, and the valve means to the pump means, thereby forming a recirculation loop for conducting spent-dialysis solution from the dialyzer through the pump means and to the tank means, and recirculating spent-dialysis solution through said valve means to said pump means.

4. A dialysis machine for drawing dialysis solution through a dialyzer under a negative pressure and for removing dissolved and entrained gases from the dialysis solution prior to delivery to the dialyzer, said machine comprising:

(a) selectively adjustable flow control valve means for controlling the volume of fresh dialysis solution flowing therethrough, (b) deairing tank means downstream of said valve means for receiving fresh dialysis solution from said valve means, said deairing tank means including: (i) dialysis solution inlet means through which fresh dialysis solution enters said deairing tank means, (ii) gas outlet means and (iii) deaerated dialysis solution outlet means associated with said dialyzer, (c) substantially constant speed and constant volume suction pump means operatively associated with said deairing tank means and positioned downstream of and connected to said dialyzer for applying a negative pressure thereto and operatively associated with said gas outlet means and said dialysis solution outlet means for drawing deaerated dialysis solution from said deairing tank means through the dialyzer to said pump means, and for drawing gas from said deairing tank means to said pump means, (d) air separation and holding tank means, positioned downstream of said pump means, for receiving said gas and only spent-dialysis solution, said separation tank means having an inlet, a drain outlet adjacent the top of the separation tank means and a recirculation outlet adjacent the bottom of the separation tank means and said separation tank means being shaped and constructed so as to permit gas and gas-containing spent-dialysis solution to exit said separation tank means through said drain outlet and to permit spent-dialysis solution with a lesser gas content to be drawn from said separation tank means through said recirculation outlet; and (e) negative pressure control valve means, positioned downstream of the separation tank means, for adjusting negative pressure in a dialyzer and cooperatively associated with said recirculation outlet and the upstream side of said pump means so that spent-dialysis solution having a lesser gas content is drawn from said recirculation tank means through said control valve means to said pump means.

5. A dialysis machine as in claim 4, wherein said deairing tank means includes internal check valve means cooperatively associated with said gas outlet means for preventing flow of dialysis solution through said gas outlet means, said check valve means adapted to sealingly engage said gas outlet means when the liquid in said tank reaches a predetermined level.

6. A dialysis machine as in claim 5, wherein said deairing tank means further includes baffle means interposed between said check valve means and said dialysis solution inlet means for preventing incoming dialysis solution from flowing directly against said check valve means and impairing the operation thereof.

7. A dialysis machine for drawing dialysis solution through a dialyzer under a negative pressure and for removing dissolved and entrained gases from the dialysis solution prior to delivery to the dialyzer, said machine comprising:
 (A) selectively adjustable flow control valve means for controlling the volume of fresh dialysis solution flowing therethrough,
 (B) deairing tank means downstream of said valve means for receiving dialysis solution from said valve means, said deairing tank means including dialysis solution inlet means through which dialysis solution enters said deairing tank means, gas outlet means and deaerated dialysis solution outlet means associated with said dialyzer,
 (C) substantially constant speed and constant volume suction pump means operatively associated with said deairing tank means and positioned downstream of and connected to said dialyzer for applying a negative pressure thereto and operatively associated with said gas outlet means and said dialysis solution outlet means for drawing deaerated dialysis solution from said deairing tank means through the dialyzer to said pump means, and for drawing gas from said deairing tank means to said pump means,
 (D) air separation and holding tank means, positioned downstream of said pump means, for receiving said gas and spent-dialysis solution, said separation tank means having an inlet, a drain outlet adjacent the top of the separation tank means and a recirculation outlet adjacent the bottom of the separation tank means, and said separation tank means being shaped and constructed so as to permit gas and gas-containing spent-dialysis solution to exit said separation tank means through said drain outlet and to permit spent-dialysis solution with a lesser gas content to be drawn from said separation tank means through said recirculation outlet; and
 (E) negative pressure control valve means, positioned downstream of the separation tank means, for adjusting negative pressure in a dialyzer and cooperatively associated with said recirculation outlet and the upstream side of said pump means so that spent-dialysis solution having a lesser gas content is drawn from said recirculation tank means through said control valve means to said pump means;
wherein said deairing tank means is elongated and adapted to be positioned in an upright attitude and has:
 (i) a hollow, elongated and tubular casing,
 (ii) end cap means for closing each end of said casing,
 (iii) said dialysis solution inlet means adjacent the upper end of the casing,
 (iv) said deaerated dialysis solution outlet means adjacent the lower end of the casing,
 (v) said outlet means in the upper end cap means, and
 (vi) an internal baffle-and-check valve assembly for closing the gas outlet means from flow when the liquid level reaches a predetermined level and for assuring the proper opening and closing of said gas outlet means, said assembly comprising:
  (a) tubular baffle means secured at one end to said end cap means, surrounding said gas outlet means and being spaced from said casing, said baffle means extending from said cap means and terminating in an open end, which is positioned between said dialysis solution inlet means and said deaerated dialysis solution outlet means;
  (b) ball-valve means positioned within said baffle means for sealingly engaging said gas outlet means,
  (c) means retaining said ball-valve means in said baffle means between said gas outlet means and said other end of said baffle means; and
  (d) said assembly being constructed so that incoming dialysis solution will flow against said baffle means and prevent direct flow against said ball-valve means.

8. A deairing tank as in claim 7, wherein said baffle means has a flow port extending therethrough adjacent said end cap means for providing communication from one side of said baffle means to the other side.

* * * * *